United States Patent [19]

Eckstein

[11] Patent Number: 4,964,304
[45] Date of Patent: Oct. 23, 1990

[54] AUDIOMETRIC TESTING METHOD AND APPARATUS

[76] Inventor: Leo K. Eckstein, 11350 Kingsland St., Los Angeles, Calif. 90066

[21] Appl. No.: 170,245

[22] Filed: Mar. 18, 1988

[51] Int. Cl.$^5$ .............................................. A61B 1/22
[52] U.S. Cl. ....................................... 73/585; 128/903
[58] Field of Search .......................... 73/585; 128/903; 340/870.01, 870.02, 870.07; 434/351

[56] References Cited

U.S. PATENT DOCUMENTS 3,122,847  3/1964  Redfield et al. ..................... 434/351
3,974,335  8/1976  Blackledge ............................. 73/585

Primary Examiner—Hezron E. Williams
Assistant Examiner—Louis M. Arana
Attorney, Agent, or Firm—Cislo & Thomas

[57] ABSTRACT

Means for transmitting an FM radio signal carrying an audio test signal to a preselected one of two receivers in the headset of a patient, together with FM signalling means carried by the patient to transmit signals to the audiometer indicating which of the patient's ears received the test signal to permit the patient to have virtually unlimited mobility during the testing procedure. Separate FM signal channels may be provided to permit simultaneous testing of a plurality of patients. Furthermore, if desired, a predetermined pattern of test signals may be recorded and means may be provided for automatically transmitting the test signals and recording the patient response signals, thereby permitting fully automatic testing to be conducted.

10 Claims, 1 Drawing Sheet

AUDIOMETRIC TESTING METHOD AND APPARATUS

BACKGROUND OF THE INVENTION

This invention relates to audiometers and is particularly directed to audiometers employing frequency modulated radio means for communicating between the testing device and one or more patients being tested.

Audiometers have long been used to test the hearing of a patient by generating audio signals at various pitches and amplitudes. Conventionally, these audio signals have been supplied to a patient by means of wires connected to the earphones of a headset worn by the patient. The pitch and amplitude of the audio signals are varied, more or less randomly, and the signals are selectively directed to one or the other of the patient's earphones, in response to which the patient is asked to indicate when they hear a signal and which ear they hear it in.

As indicated above, the prior art audiometers have communicated the test signals to the patient by means of wires. However, this means that the wires of the patient's headset must be physically connected to the test device, which greatly limits the mobility of the patient and restricts the number of patients who can be tested at a given time.

A search in the U.S. Patent Office has revealed the following:

| U.S. Pat. No. | Inventor | Issued |
| --- | --- | --- |
| 3,808,354 | M. Feezor | April 30, 1974 |
| 3,809,811 | J. Delisle et al | May 7, 1974 |
| 3,906,158 | J. D. Lake | Sept. 16, 1975 |
| 3,974,335 | V. O. Blackledge | Aug. 10, 1976 |
| 4,109,106 | R. Voss | Aug. 22, 1978 |
| 4,157,456 | R. Voss | June 5, 1979 |
| 4,334,315 | H. Ono et al | June 8, 1982 |
| 4,539,708 | E. G. Norris | Sept. 3, 1985 |
| 4,369,521 | T. Sawada | June 18, 1983 |
| 4,667,683 | R. S. Dugot | May 26, 1987 |

The patents to Voss, Lake and Blackledge each relate to audiometric devices which communicate with the patient by means of wires. The patent to Ono et al teaches the use of miniaturized frequency modulated (FM) radio equipment for various communication applications, but does not suggest that it would have any use in audiometric testing. The remaining patents are of general interest only.

OBJECTS AND SUMMARY OF THE INVENTION

The present invention provides means for transmitting an FM radio signal carrying an audio test signal to a pre-selected one of two receivers in the headset of a patient, together with FM signaling means carried by the patient to transmit signals to the audiometer indicating whether he has heard a signal of a given level emitted by the audiometer. This permits the patient to have virtually unlimited mobility during the testing procedure. Moreover, many patients may be provided with their own audio frequency modulated FM hand held signaling means and may respond to the audiometric signals to permit simultaneous testing of a plurality of patients. Furthermore, if desired, a predetermined pattern of test signals may be recorded and means may be provided for automatically transmitting the test signals and recording the patient response signals, thereby permitting fully automatic testing to be conducted.

Accordingly, it is an object of the present invention to provide improved audiometric testing means.

Another object of the present invention is to provide audiometric testing means using wireless communication between the testing device and the patient.

A further object of the present invention is to provide audiometric testing means using FM radio communication between the testing device and the patient.

An additional object of the present invention is to provide means for simultaneous audiometric testing of a plurality of patients.

Another object of the present invention is to provide audiometric testing means which permits the patient to have virtually unlimited mobility during the testing procedure.

A further object of the present invention is to provide means for fully automatic audiometric testing of patients.

A specific object of the present invention is to provide means for transmitting an FM radio signal carrying an audio test signal to a preselected one of two channels of a receiver in the headset of a patient, together with FM signaling means carried by the patient to transmit signals to the audiometer indicating which of the patients received the test signal.

An additional specific object of the present invention is to provide means for transmitting an FM radio signal carrying audiometric test signals to a plurality of patients' headsets, together with a plurality of FM signalling means each carried by a respective patient and each transmitting specific audio signals on an FM channel to a common receiver to permit simultaneous audiometric testing of a plurality of patients.

A further specific object of the present invention is to provide means for recording a predetermined audiometric test pattern together with means for transmitting an FM radio signal carrying audiometric test signals to a plurality of patients' headsets, and a plurality of FM signaling means each carried by a respective patient and each transmitting respective audio signals on a given FM channel to a common receiver to permit simultaneous, fully automatic audiometric testing of a plurality of patients.

These and other objects and features of the present invention will be apparent from the following detailed description, taken with reference to the figures of the accompanying drawings.

DETAILED DESCRIPTION OF THE INVENTION

Figure 1:
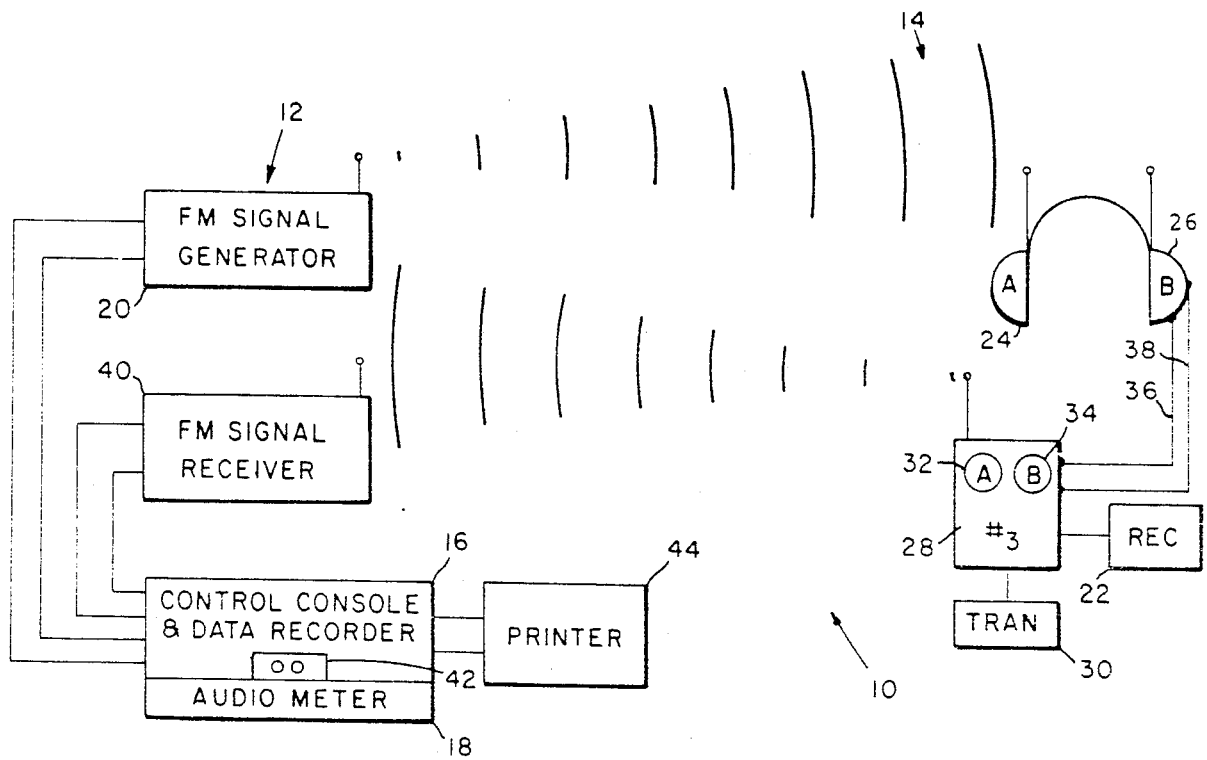
FIG. 1 is a diagrammatic representation showing an FM audiometer system embodying the present invention.

In that form of the present invention chosen for purposes of illustration in the drawing, FIG. 1 shows an audiometer system, indicated generally at 10, having a base unit 12 and a remote unit 14. Briefly, the base unit 12 is the control unit from which the audiometric testing is administered, while the remote unit 14 comprises a headset which enables the patient to receive the test signals, together with a signalling pad which permits the patient to transmit signals to the base unit as described below.

The base unit 12 comprises a control console 16 which determines the audiometric test signals to be generated by an audiometer 18 and supplies these test signals to modulate the output of a two-channel, frequency-modulated (FM) radio transmitter 20. As is well known, frequency modulation means that the transmitter 20 generates a carrier signal at a predetermined frequency, for example, 100 mc, and the modulating signal from the audiometer 18 serves to deviate the carrier frequency plus or minus by an amount corresponding to the strength or amplitude of the modulating signal from the audiometer 18. It should be noted that amplitude of the FM radio signal is not the determining factor in establishing the loudness of the demodulated audio signal which is received by the patient. Thus, variations in the distance between the base unit 12 and the remote unit 14 are immaterial within a given range.

As stated above, the transmitter 20 is a two channel device and the control console 16 determines which of the two channels will carry the audiometric test signals. The remote unit 14 comprises a two-channel FM receiver 22 which receives the modulated signal from the transmitter 20, demodulates it and supplies the audiometric test signal to one or the other of a pair of earphones 24 and 26, depending upon which FM channel carried the signal. The remote unit 14 also comprises a handpad 28 containing an FM transmitter 30 and two buttons, as seen at 32 and 34. When the patient hears an audio signal in one of the earphones 24 or 26, the patient indicates this by pressing the corresponding one of the buttons 32 or 34 to cause the transmitter 30 to send a signal to the base unit 12 indicating that the patient was heard the test signal and in which ear the signal was heard. As seen in FIG. 1, the receiver 22 and the transmitter 30 are both located in the handpad 28 of the remote unit 14 and the earphones 24 and 26 are connected to the handpad 28 by wires 36 and 38. However, it will be apparent to those skilled in the art that, if desired, the receiver 22 could be mounted on the handset with the earphones 24 and 26, in which case, the wires 36 and 38 could be eliminated and the handpad 28 could be physically independent of the handset.

At the base unit 12, the signals from the transmitter 30 of the remote unit 14 are received by FM radio receiver 40 and are demodulated and supplied to the console 16 which displays the results on a suitable display means 42 and records the results on a suitable recorder, as seen at 44.

Since communication between the base unit 12 and the remote unit 14 is by radio, no wires are required to connect the units 12 and 14. Moreover, as noted above, the loudness of the audio signals received by the remote unit 14 are unrelated to the distance between the base unit 12 and the remote unit 14 and, hence, the patient using the remote unit 14 has virtually unrestricted freedom of movement during the testing procedure and can sit where he chooses. It should also be understood that the FM radio signals from the transmitter 20 can be received simultaneously by a plurality of remote units, such as the remote unit 14, without conflict or interference. Thus, if desired, a plurality of patients may be tested simultaneously by providing each of the patients with a respective remote unit, corresponding to the remote unit 14 of FIG. 1. When this is done, the transmitter 30 of each of the remote units 14 would be made to transmit on their respective audio frequency modulated FM frequency and the receiver 40 of the base unit 12 would be a multichannel two-modulated FM receiver so that it could isolate the signals from each of the remote units 14 according to the audio filter channel on which the signals were received. The display means 42 and recorder 44 would separately indicate the signals received on each of the audio channels and, since each channel would correspond to a respective one of the remote units 14, it would be easy to determine which remote unit 14 had sent which signals.

It would also be possible to provide a predetermined pattern of audiometric test signals, by means of a tape recorder, computer or the like, and to provide means in the control console 16 for transmitting the predetermined test pattern automatically and, if desired, repeatedly. With this arrangement, it would not even be necessary for the test operator to be present. Means could easily be provided in the remote unit 14 to provide a signal to the base unit 14 to indicate the start and finish of a given patient's use of the system and, since the base unit 12 separately records the signals received from the respective remote units 14, it would be easy for the test operator to subsequently identify which test results related to which patient. Thus, audiometric testing could be conducted on a fully automatic basis on a plurality of patients simultaneously.

Figure 2:
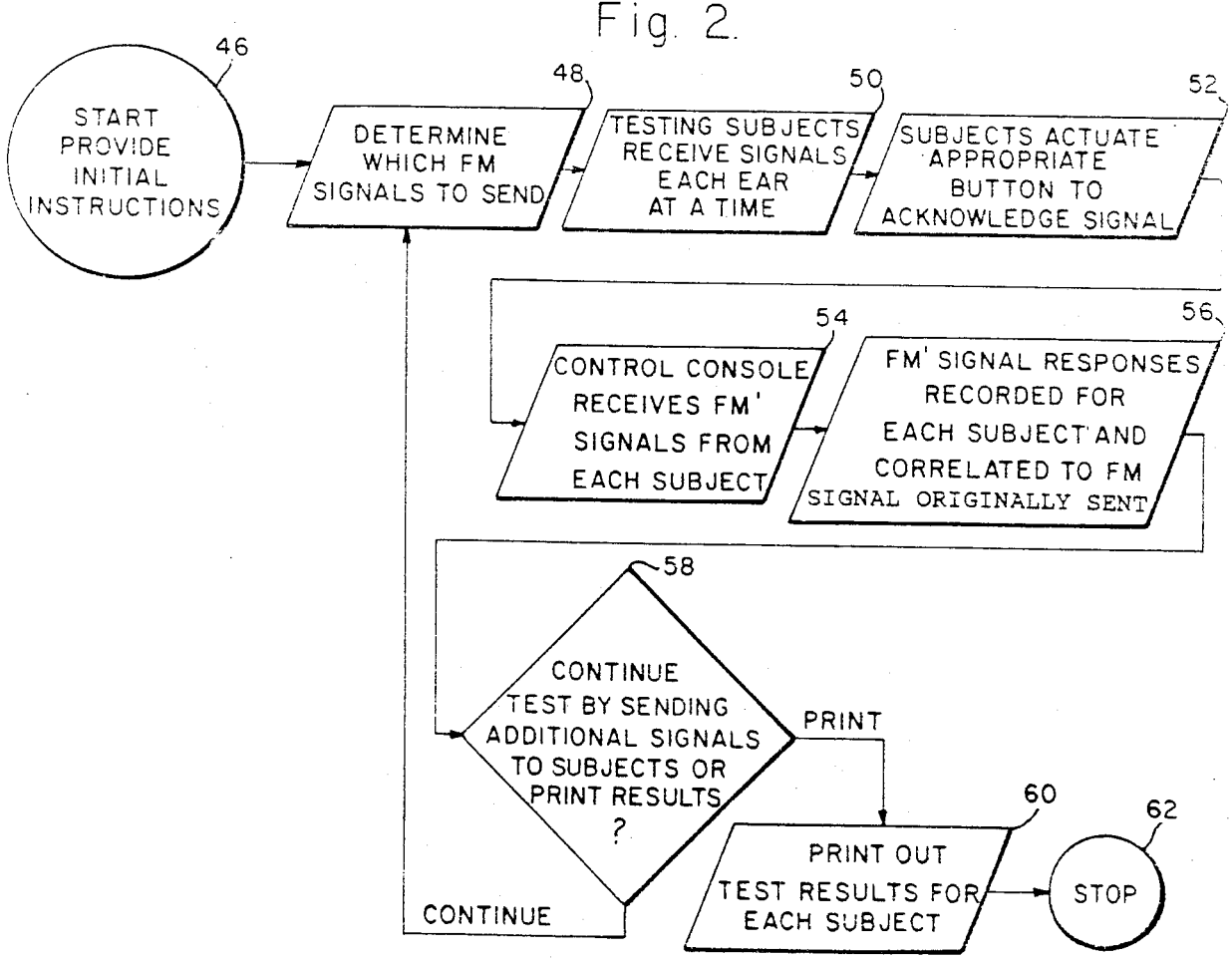
FIG. 2 is a flow diagram showing the steps involved in testing a patient with the audiometer system of FIG. 1.

FIG. 2 is a flow diagram showing the steps involved in testing a patient with the audiometer system of FIG. 1. As shown in block 46, the procedure begins with the test operator providing the initial instructions to the system and to the patient. In the case of the fully automatic testing, this would include provision of the predetermined audiometric test pattern by tape recording, computer programming or the like, and provision of instructions to the patient, as by a printed card. Next, as seen in block 48, the test operator or the predetermined test pattern will cause the transmitter 20 of the base unit 12 to send a signal on an appropriate signal channel, for example, to send a signal to the right earphone 26 of the remote unit 14. Block 50 indicates that the patient receives the test signal and, if the patient hears the signal, they respond by activating the appropriate one of the buttons 32 or 34 on the handpad 28, as indicated in block 52, to cause the transmitter 30 of the remote unit 14 to send the appropriate response signal to the base unit 12. At the base unit 12, FM receiver 40 receives the signals from each of the remote units 14, as indicated in block 54, and passes the demodulated response signals to the console 16. Within the console 16, the incoming response signals are separated, if more than one remote unit 14 is employed, and the console 16 then correlates the response signals with the test signal to which the response relates and displays the results on the display means 42, as indicated in block 56.

Next, as seen in block 58, a decision is made, either by the test operator or by the predetermined test pattern, to either continue or terminate the test procedure. If the test is to continue, the system returns to block 48 to determine the next test signal to be transmitted. Where the testing is conducted on a fully automatic basis, the predetermined test pattern may be made to provide a sequence of audiometric test signals and to repeat this sequence continuously as long as required and patients maY begin their testing at any point in the sequence by activating a respective one of the remote units 14. Alternatively, when the testing is completed, the test results will be recorded, as indicated in block 60 and the procedure will be terminated, as indicated in block 62.

As described above, the audiometric testing system of the present invention may be employed equally well with one or a plurality of patients simultaneously. Moreover, the system may be controlled by a test operator who is present when the testing occurs or, if desired, the system may be made to conduct audiometric testing on a fully automatic and repetitive basis. Obviously, numerous other variations and modifications may be made without departing from the present invention. Therefore, it should be clearly understood that the form of the present invention described above and shown in the accompanying drawings is illustrative only and is not intended to limited the scope of the present invention.

I claim:

1. An audiometer comprising:
   means for transmitting an FM radio signal carrying an audiometric test signal on a selected one of a pair of radio transmitting channels; and,
   FM receiver means for receiving said FM radio signal on one of a pair of radio receiving channels, said FM receiver means including a pair of earphones, wherein each earphone of said pair of earphones is coupled to a respective one of said pair of radio receiving channels for separately applying said audiometric test signal to a patient's ears.

2. An audiometer system comprising:
   (a) a base unit including an FM radio transmitter, said FM transmitter having two channels;
   (b) modulating means for modulating the output of said transmitter with audiometric test signals; and,
   (c) a remote unit including (1) an FM receiver having two channels, and (2) a pair of earphones, each of said earphones being coupled to a respective one of said two FM receiver channels, whereby an audio signal is applied to one or the other of said earphones responsive to a selected one of said two FM transmitter channels carrying said audiometric test signals.

3. The system of claim 2 further comprising: FM transmitter means located at said remote unit having means to enable said patient to indicate which of said earphones supplied an audio signal; and an FM receiver located at said base unit to receive the signals from said transmitter at said remote unit.

4. The system of claim 3 further comprising: a plurality of said remote units.

5. The system of claim 4 further comprising: means included in the transmitter of said remote unit for identifying the signals from that unit; and means included in the receiver at said base unit for separating the signals from each of said remote units.

6. The system of claim 3 further comprising: means located at said base unit for displaying an indication of the signals from said remote unit.

7. The system of claim 6 further comprising: means for displaying an indication of the signals transmitted by the transmitter at said base unit.

8. The system of claim 5 further comprising: means located at said base unit for separately displaying an indication of the signals received from each of said remote units and for correlating the displays of said signals with an indication of the signals transmitted by said base unit.

9. The system of claim 2 further comprising: means included in the modulating means at said base unit for modulating the output of said transmitter with a predetermined pattern of audiometric signals.

10. The system of claim 9 further comprising: means for continuously repeating said pattern.

* * * * *

UNITED STATES PATENT AND TRADEMARK OFFICE
CERTIFICATE OF CORRECTION

PATENT NO. : 4,964,304

DATED : Oct. 23, 1990

INVENTOR(S) : Leo H. Eckstein

It is certified that error appears in the above-identified patent and that said Letters Patent is hereby corrected as shown below:

ON TITLE PAGE:

Item [76[  Inventor should read "Leo H. Eckstein".

Signed and Sealed this

Twenty-third Day of June, 1992

Attest:

DOUGLAS B. COMER

Attesting Officer

Acting Commissioner of Patents and Trademarks